(12) United States Patent
Olier

(10) Patent No.: US 9,932,301 B2
(45) Date of Patent: Apr. 3, 2018

(54) POLYACRYLATE ALLOPHANATE

(71) Applicant: VENCOREX FRANCE, Saint-Priest (FR)

(72) Inventor: Philippe Olier, Lyons (FR)

(73) Assignee: VENCOREX FRANCE, Saint-Priest (FR)

( * ) Notice: Subject to any disclaimer, the term of this patent is extended or adjusted under 35 U.S.C. 154(b) by 0 days.

(21) Appl. No.: 14/776,055

(22) PCT Filed: Mar. 14, 2014

(86) PCT No.: PCT/EP2014/055052
§ 371 (c)(1),
(2) Date: Sep. 14, 2015

(87) PCT Pub. No.: WO2014/140238
PCT Pub. Date: Sep. 18, 2014

(65) Prior Publication Data
US 2016/0024002 A1      Jan. 28, 2016

(30) Foreign Application Priority Data

Mar. 14, 2013   (FR) ..................... 13 52300

(51) Int. Cl.
| | | |
|---|---|---|
| *C07C 275/60* | (2006.01) | |
| *C09D 4/00* | (2006.01) | |
| *C08G 18/67* | (2006.01) | |
| *C08G 18/78* | (2006.01) | |
| *C08F 290/06* | (2006.01) | |

(52) U.S. Cl.
CPC ........ *C07C 275/60* (2013.01); *C08F 290/067* (2013.01); *C08G 18/672* (2013.01); *C08G 18/7837* (2013.01); *C09D 4/00* (2013.01)

(58) Field of Classification Search
CPC ...... C07C 275/60; C09D 4/00; C08G 18/672; C08G 18/7837; C08F 290/067
USPC ....................................... 560/159
See application file for complete search history.

(56) References Cited

U.S. PATENT DOCUMENTS

| | | |
|---|---|---|
| 6,426,414 B1 | 7/2002 | Laas et al. |
| 6,753,394 B2 | 6/2004 | Weikard et al. |
| 8,106,140 B2 | 1/2012 | Ludewig et al. |
| 2003/0050390 A1 | 3/2003 | Weikard et al. |
| 2007/0191570 A1 | 8/2007 | Weikard et al. |
| 2009/0062500 A1 | 3/2009 | Ludewig et al. |
| 2009/0137750 A1 | 5/2009 | Ludewig et al. |
| 2010/0010113 A1* | 1/2010 | Schwalm ........... C08G 18/0823 522/86 |
| 2010/0101331 A1 | 4/2010 | Lincoln et al. |
| 2010/0204434 A1 | 8/2010 | Ludewig et al. |
| 2010/0273938 A1 | 10/2010 | Martin-Portugues et al. |
| 2012/0016073 A1 | 1/2012 | Bernard et al. |

FOREIGN PATENT DOCUMENTS

| | | |
|---|---|---|
| JP | 11349805 A | 12/1999 |
| JP | 200683273 A | 3/2006 |
| JP | 201252019 A | 3/2012 |
| WO | 2008145932 A1 | 12/2008 |
| WO | 2010067005 A1 | 6/2010 |

OTHER PUBLICATIONS

Sharmin et al. Polyurethane: An Introduction. InTech. (open science) p. 3-16, 2012. http://dx.doi.org/10.5772/51663 Published: Aug. 29, 2012.*
The Search Report issued by EPO as the International Searching Authority dated Jun. 20, 2014.

* cited by examiner

*Primary Examiner* — Yih-Horng Shiao
(74) *Attorney, Agent, or Firm* — Michael B. Fein; Eckert Seamans Cherin & Mellot, LLC

(57) ABSTRACT

The invention relates to a modified allophanate compound bearing acrylate functions, resulting from the reaction of a particular allophanate with an ester from the reaction between an acid selected from acrylic acid and methacrylic acid and at least one polyol that does not contain an oxylakylene or aa (poly)oxyalkylene group. The invention further relates to the use of said modified allophanate for preparing a hydrophobic cross-linkable coating composition by means of UV radiation.

21 Claims, 1 Drawing Sheet

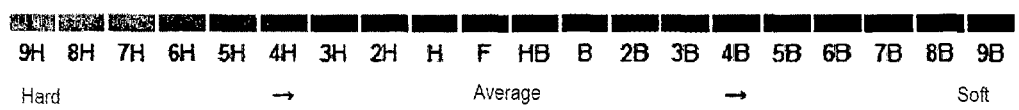
9H 8H 7H 6H 5H 4H 3H 2H H F HB B 2B 3B 4B 5B 6B 7B 8B 9B
Hard → Average → Soft

POLYACRYLATE ALLOPHANATE

CROSS-REFERENCE TO RELATED APPLICATIONS

This application is the U.S. national stage of PCT/EP2014/055052 filed Mar. 14, 2014, which claims priority from French application 1352300 filed Mar. 14, 2013, both of which are hereby incorporated by reference.

The invention relates to a modified allophanate compound and bearing acrylate functions, resulting from the reaction of a particular allophanate with an ester, resulting from the reaction between an acid selected from acrylic acid and methacrylic acid, and at least one alcohol not comprising any oxyalkylene or (poly)oxyalkylene group.

The invention also relates to the use of this modified allophanate for preparing a hydrophobic coating composition, in particular crosslinkable by UV irradiation.

Allophanates intended for coating compositions are known. WO-2010/067005 describes a method for preparing allophanate as well as an allophanate and a composition comprising the allophanate and intended for preparing coating, in particular paint compositions.

Apart, from U.S. Pat. No. 6,753,394, cross-linkable urethane-acrylates are known and prepared from a mixture of oxyalkyl-polyols and of diisocyanates or polyisocyanates and of an ester of acrylic or methacrylic acid.

US-2010/273938 describes polyisocyanates comprising allophanate groups and prepared from isophorone diisocyanate (IPDI). Polymerized acrylate resins which are disclosed in this document do not comprise free acrylate functions and therefore cannot react under UV irradiation.

US-2010/204434 describes the preparation of unsaturated allophanates which may be used for preparing coatings. In order to be able to control the viscosity, the curable compositions described in this document require the systematic presence of isocyanate compounds modified by means of caprolactones. These compositions do not allow the control of the hydrophobicity of the prepared coatings.

However, there exists a need for other solutions for preparing cross-linkable hydrophobic coating compositions.

Indeed, the compositions of the state of the art are generally sensitive to ageing and to oxidation because of the presence of ethylene oxide groups.

Another frequently encountered problem with the compositions of the state of the art is that they lead to coatings sensitive to water and to humidity because of the presence of polyether groups. These coatings generally have insufficient hydrophobicity.

Another problem encountered with the isocyanate-acrylate coating compositions of the state of the art is related to their too high viscosity.

The solutions of the state of the art then consist of using a diluent or a reactive diluent, for example in the form of another compound with acrylate or methacrylate functions but which are known for having toxicity problems.

Another known solution also consists of using polyols comprising oxyalkylene functions.

Another major problem of isocyanate-acrylates of the state of the art is related to the application during their preparation, of substrates, notably of isocyanate monomers, which are toxic and which have sanitary problems.

Another drawback of the known isocyanate-acrylates is their low ratio between the number of isocyanate functionalities which they contain, relatively to their viscosity. Indeed, the isocyanate-acrylates of the state of the art which contain a large number of urethane functions are often too viscous for being used in an efficient way.

Therefore there exists a need for compositions based on isocyanate-acrylates having improved properties.

There also exists a need for such compositions which allow preparing coatings not having the problems of the coatings prepared by means of compositions of the state of the art.

Thus, the invention provides a modified allophanate which allows providing solutions to all or part of the problems of isocyanate-acrylates of the state of the art.

The modified allophanate according to the invention is particularly advantageous for its reduced viscosity while avoiding the application of monomers to be avoided because of their toxicity.

The modified allophanate according to the invention is also particularly advantageous for preparing coating compositions for which scratch resistance is improved.

Further, the modified allophanate according to the invention allows preparations of coating compositions for which hydrophobicity is improved. Measurement of the contact angles of the formed coatings is thus a particularly advantageous feature obtained during the application of the modified allophanate according to the invention during the preparation of coating compositions.

The invention relates to a modified allophanate and prepared or which may be prepared according to the method comprising (a) the preparation of an allophanate of formula (I)

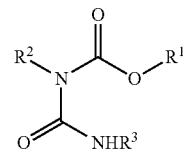

(I)

wherein $R^1$ represents the radical of a monoalcohol compound and comprising an ether or polyether function after reaction of hydrogen of the OH function of the monoalcohol with a compound with an isocyanate function;

$R^2$ and $R^3$, either identical or different, represent a hydrocarbon group, comprising a derivatized or non-derivatized isocyanate function; and then (b) the reaction with at least one ester
hydroxy-functionalized;
comprising at least one acrylate function and
prepared or which may be prepared by reaction between an acid selected from among acrylic acid and methacrylic acid and at least one alcohol.

According to the present invention, a non-derivatized isocyanate function is a free isocyanate function for which the NCO group is accessible. A derivatized isocyanate function is a function for which the NCO group is bound to another chemical group.

The modified allophanate according to the invention therefore comprises at least one acrylate function. Preferably, it comprises several acrylate functions. For this modified allophanate according to the invention, the acrylate functions are bound to the chemical radical from the allophanate of formula (I) via the chemical radical of the applied ester. The acrylate functions are therefore not directly bound to the chemical radical of the allophanate of formula (I).

Preferably, within the modified allophanate according to the invention, the molar ratio of the urethane/allophanate functions is equal to 2.

Generally, the NCO functionality of the allophanate of formula (I) according to the invention is equal to 2+/−5%. This functionality may actually have slight variability around the value 2, notably depending on the particular conditions for preparing this allophanate of formula (I).

Advantageously, the modified allophanate according to the invention is prepared from an allophanate of formula (I) which has an NCO functionality selected from an NCO functionality ranging from 1.9 to 2.3; an NCO functionality ranging from 1.9 to 2.2; an NCO functionality ranging from 1.9 to 2.1; an NCO functionality ranging from 2 to 2.3; an NCO functionality ranging from 2 to 2.2.

Preferably for the allophanate of formula (I), $R^1$ represents the radical of a monoalcohol compound not comprising any acrylate function.

Advantageously for the allophanate of formula (I) according to the invention, $R^1$ represents the radical of a monoalcohol compound which is a hydrocarbon compound comprising a hydroxyl function.

An alcohol with an aliphatic chain including alcohols with a cycloaliphatic chain or preferably an alcohol with a linear or slightly branched alkyl chain comprising a single OH function are advantageously used. This may be a heterocyclic alcohol of the oxetane type.

The suitable alcohols may also optionally comprise one or several double bonds.

The monoalcohol used for preparing the allophanate of formula (I) according to the invention comprises an ether or polyether function, advantageously an alkylene (poly)oxide function, preferably ethylene (poly) oxide, notably ethylene polyoxide monoether, advantageously including at most 25 ethylene oxide links on average and preferentially including at most 10 ethylene oxide links on average.

Other particularly advantageous alcohols, notably from the point of view of low viscosity, are the compounds of formula $R^a$—[O—CH($R^b$)—CH$_2$]$_t$—OH, wherein $R^a$ represents a linear or branched $C_1$-$C_{20}$-alkyl group or a group of formula $R^c$—CO— in which $R^c$ represents a linear or branched $C_1$-$C_{20}$-alkyl group; $R^b$ independently represents H or an alkyl group, preferably a $C_1$-$C_8$ alkyl group, notably methyl, or a polyether group, notably a group of formula —CH$_2$O$R^d$ wherein $R^d$ represents a hydrocarbon chain, notably a polyoxyalkylene, chain, preferably polyoxyethylene; t represents an integer, advantageously an integer ranging from 1 to 10, preferably from 1 to 5.

More particularly advantageous alcohols are the compounds of formula $R^a$—[O—CH($R^b$)—CH$_2$]$_t$—OH, wherein $R^a$ represents a linear or branched $C_1$-$C_{20}$-alkyl group or a group of formula $R^c$—CO— wherein $R^c$ represents a linear or branched $C_1$-$C_{20}$-alkyl group; $R^b$ independently represents H, a methyl group or a group of formula —CH$_2$O$R^d$ wherein $R^d$ represents a polyoxyethylene chain; t represents an integer ranging from 1 to 5.

As preferred monoalcohols, mention may be made of $C_{12}$-$C_{18}$ monoalcohols with 30 ethylene oxide functions ($C_{12}$-$C_{18}$ (30EO)—OH), in particular from mixtures of $C_{12}$-$C_{18}$ alcohols, of $C_{14}$-$C_{18}$ alcohols and of $C_{16}$-$C_{18}$ alcohols. These $C_{12}$-$C_{18}$, $C_{14}$-$C_{18}$ and $C_{16}$-$C_{18}$ alcohols may also be used alone.

As particular examples of such monoalcohols, mention may be made of the compounds selected from among the compound CAS RN 68213-23-0, the compound CAS RN 68154-96-1 and the compound CAS RN 68439-49-6 which may be used alone or in mixtures.

The aliphatic chain of the monoalcohol compound may further be substituted or interrupted with a cycloalkyl or heterocyclic group in which the OH function may be directly bound to a carbon atom of the hydrocarbon ring or of the heterocycle.

The derivatives of the silanol type may also be suitable as a compound at the origin of the group $R^1$ of the allophanate of formula (I).

Advantageously, the monoalcohol at the origin of the $R^1$ group comprises on average less than 5 alkylene oxide links, preferably on average 2 or 3 alkylene oxide links. It is thus possible to increase the NCO content of the allophanate of formula (I).

Upon preparing the allophanate of formula (I), it may be advantageous to use a mixture of compounds with different alcohol functions. Advantageously, as alcohols only monoalcohols are applied.

During the preparation of the allophanate of formula (I), it may also be advantageous to use several different monoalcohols, for example at least 3 different monoalcohols, preferably at least 8 different monoalcohols.

In addition to the monoalcohols, other alcohols of a different type may be applied. For example mention may be made of alkyl alcohols with a linear $C_1$-$C_{10}$ chain, in particular $C_4$-$C_8$ alcohols.

For the allophanate of formula (I), the groups $R^2$ and $R^3$ may comprise a derivatized or non-derivatized isocyanate function which is able to form urethane functions by reaction with a compound bearing a labile hydrogen atom, in particular by reaction with an alcohol.

According to the invention, for the allophanate of formula (I), $R^2$ and $R^3$, either identical or different, preferably represent a group comprising a derivatized or non-derivatized isocyanate function and selected from among an aliphatic, cycloaliphatic, heterocyclic or aromatic hydrocarbon group, preferably an aliphatic hydrocarbon group comprising a derivatized or non-derivatized isocyanate function.

For the modified allophanate according to the invention, the allophanate of formula (I) is a homo-allophanate and $R^2$ and $R^3$ are identical or else the allophanate of formula (I) is a mixed allophanate and $R^2$ and $R^3$ are different.

According to the invention, the allophanate of formula (I) may be selected from a bis-allophanate, a tris-allophanate, the preparation of a mixture of other allophanates selected from among one or several heavy allophanates, as well as the preparation in a minority way, of isocyanate $R^2$NCO and alcohol $R^1$OH carbamate or of isocyanate $R^3$NCO and alcohol $R^1$OH carbamate or carbamate of $R^2$NCO and $R^3$NCO isocyanates and alcohol $R^1$OH.

Preferably, the allophanate of formula (I) is prepared from hexamethylene diisocyanate (HDI) or isophorone diisocyanate (IPDI).

In a sometimes advantageous way, the preparation of the modified allophanate according to the invention may comprise the preparation (a) of an allophanate of formula (I) and also the preparation of at least one polyfunctional isocyanate.

As a polyfunctional isocyanate, mention may be made of polyfunctional isocyanates as tricondensates, in particular the compounds of formula (II), as well as the polyfunctional isocyanates from the condensation of several compounds of formula (II):

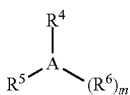
(II)

wherein $R^4$, $R^5$ and $R^6$ represent independently an aliphatic, cycloaliphatic, heterocyclic or aromatic hydrocarbon or heterocarbon group comprising a derivatized or non-derivatized isocyanate function;

m represents 0, 1 or 2;

A represents a group selected from an isocyanurate group, an imino oxadiazine dione group, an oxadiazine trione group, a biuret group, of formulae (A1) to (A4), respectively

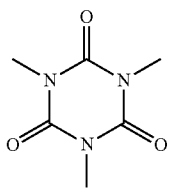
(A1)

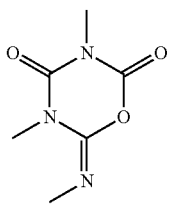
(A2)

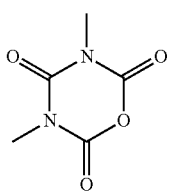
(A3)

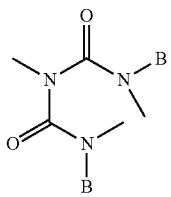
(A4)

wherein B represents independently a hydrogen atom; a hydrocarbon group, notably a $C_1$-$C_{20}$ hydrocarbon group; a heterocarbon group comprising at least one heteroatom selected from O, N, S, Si, notably a heterocarbon $C_1$-$C_{20}$ group comprising at least one heteroatom selected from O, N, S, Si; a group of formula (B1)

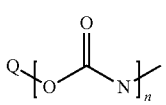
(B1)

wherein n represents 3 or 4 and Q represents a group selected from a hydrocarbon group, an alkyl group, a hydrocarbon group, an aliphatic, cycloaliphatic, heterocyclic or aromatic heterocarbon group, comprising a derivatized or non-derivatized isocyanate function.

Preferably according to the invention, the polyfunctional isocyanate as a tricondensate is a polyisocyanate isocyanurate.

One will refer to a polyfunctional isocyanate tricondensate, when $R^4$, $R^5$, $R^6$ either identical or different, represent a group of formula -A-X wherein A represents a hydrocarbon chain, i.e. including at least carbon and hydrogen and X being a hydrogen atom or an NCO group, preferably X represents an NCO group.

In other words, by polyfunctional isocyanate tricondensate are meant products from theoretical (cyclo)condensation products obtained by condensation of three moles of monomers, advantageously isocyanates, preferably diisocyanates or even triisocyanates (either identical or different), except for compounds from the condensation of more than four monomers or including allophanate groups, as well as the isocyanurate oligomers obtained by oligomerisation of (poly)isocyanate isocyanurates.

The polyfunctional isocyanate tricondensate advantageously has the characteristics:
(i) the weight ratio between the allophanate of formula (I) and the polyfunctional isocyanate tricondensate ranges from 60/40 to 90/10, from 30/70 to 90/10, from 60/40 to 80/20, from 30/70 to 80/20, from 60/40 to 85/15 or from 30/70 to 85/15;
(ii) the polyfunctional isocyanate tricondensate is produced from a tricondensation reaction for which the transformation rate of the isocyanate monomer(s), either identical or different, into a polyfunctional polyisocyanate tricondensate is greater than 8% or greater than 10% or greater than 15%;
(iii) the polyfunctional isocyanate tricondensate comprises between 1 and 99% by weight of biuret or between 2 and 75% by weight of biuret;
(iv) the combinations (i) and (ii), (i) and (iii), (ii) and (iii) or (i), (ii) and (iii).

The preparation of the modified allophanate according to the invention may comprise the preparation (a) of an allophanate of formula (I) and the preparation of at least one polyfunctional isocyanate in a proportion of less than 10% by mass based on the allophanate of formula (I); in a proportion of less than 8% by mass based on the allophanate of formula (I); in a proportion less than 6% by mass based on the allophanate of formula (I); in a proportion less than 2% by mass based on the allophanate of formula (I).

Preferably, the modified allophanate according to the invention is prepared from the allophanate of formula (I) and in the absence of polyfunctional isocyanate.

Advantageously, the preparation of the modified allophanate comprises (a) the preparation of an allophanate of formula (I) according to the invention and the reaction (b) with at least one ester produced with a single ester or with two esters.

During the reaction (b), the allophanate of formula (I) is already formed beforehand and this reaction (b) therefore does not comprise any allophanatation of the urethane applied beforehand.

During the application of the reaction (b), the allophanatation catalyst is therefore generally not more present in the reaction medium in an active form. The allophanatation catalyst is generally neutralized.

Advantageously, the ester applied during the reaction (b) of the method for preparing the modified allophanate according to the invention is prepared from an alcohol not comprising any oxyalkylene or (poly)oxyalkylene group, in particular from an alcohol not comprising any oxyethylene or (poly)oxyethylene group.

This ester may be prepared from an alcohol selected from the compounds of formula (III)

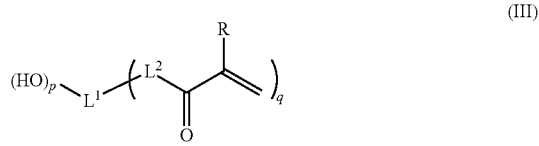

wherein p represents 1, 2, 3, 4 or 5;

$L^1$ represents a linear or branched hydrocarbon radical, or a linear or branched radical comprising a hydrocarbon chain and at least one heteroatom;

$L^2$ represents O, S or a group of formula NT wherein T represents H or a linear or branched $C_1$-$C_8$-alkyl group and N represents a nitrogen atom;

R, identical or different, represents H or a linear or branched $C_1$-$C_8$-alkyl group;

q represents 1, 2, 3, 4 or 5.

Preferably, the alcohol may be selected from among the compounds of formula (III) wherein p represents 1 or 2, in particular 1; q represents 3; $L^1$ represents a linear or branched radical, comprising one or several ether functions or a compound of formula (III) combining these features.

The ester may also be formed from a mixture of compounds, the average formula of which is a compound of formula (III).

As an example of an alcohol applied during the preparation of the ester of reaction (b) according to the invention, mention may be made of trimethyl-ol-propane (TMP).

Preferably, the reaction (b) is applied with at least one ester which is monohydroxy-functionalised.

Also preferably, the reaction (b) is applied with at least one ester selected from among 2-hydroxyalkyl(meth)acrylates, 2-hydroxyethyl(meth)acrylate, 2-hydroxypropyl(meth)acrylate, 3-hydroxypropyl(meth)acrylate, 4-hydroxybutyl(meth)acrylate, 3-hydroxy-2,2-dimethylpropyl(meth)acrylate, 2-hydroxyethyl acrylate, 2-hydroxypropyl acrylate, a caprolactone modified by esterification with hydroxyalkyl (meth)acrylates, an ϵ-caprolactone modified by esterification with hydroxyalkyl(meth)acrylates, an ϵ-caprolactone modified by esterification with hydroxyalkylacrylates, an ϵ-caprolactone modified by esterification with 2-hydroxyalkyl(meth)acrylates, an ϵ-caprolactone modified by esterification with 2-hydroxyalkylacrylates, caprolactone triacrylate, glycerol di(meth)acrylate, trimethylolpropane di(meth)acrylate, pentaerythritol tri(meth)acrylate, di(pentaerythritol) penta(meth)acrylate, trimethylol-propane diacrylate.

More preferably, the reaction (b) is applied with at least one ester selected from among 2-hydroxyalkyl(meth)acrylates, 2-hydroxyethyl(meth)acrylate, 2-hydroxypropyl(meth)acrylate, 3-hydroxypropyl(meth)acrylate, 4-hydroxybutyl-(meth)acrylate, 3-hydroxy-2,2-dimethylpropyl(meth) acrylate, 2-hydroxyethyl acrylate, 2-hydroxypropyl acrylate, glycerol di(meth)acrylate, trimethylolpropane di(meth)acrylate, pentaerythritol tri(meth)acrylate, di(pentaerythritol) penta(meth)acrylate, trimethylol-propane diacrylate.

Preferably, the ester is selected from pentaerythritol triacrylate, dipentaerythritol pentaacrylate (DPHA) and trimethylolpropane diacrylate.

In a particular advantageous way, the allophanate modified according to the invention has a viscosity measured at 25° C. comprised in the following viscosity ranges: from 500 to 200,000 mPa·s; from 500 to 150,000 mPa·s; from 500 to 120,000 mPa·s; from 500 to 100,000 mPa·s; from 500 to 30,000 mPa·s; from 500 to 50,000 mPa·s; from 500 to 15,000 mPa·s; from 1,000 to 200,000 mPa·s; from 1,000 to 150,000 mPa·s; from 1,000 to 120,000 mPa·s; from 1,000 to 100,000 mPa·s; from 1,000 to 30,000 mPa·s; from 1,000 to 15,000 mPa·s; from 2,000 to 100,000 mPa·s; from 2,000 to 50,000 mPa·s; from 2,000 to 30,000 mPa·s; from 3,000 to 30,000 mPa·s; from 3,000 to 15,000 mPa·s.

The invention also relates to the use of a modified allophanate according to the invention for preparing a coating composition, in particular a cross-linkable coating composition, notably a coating composition which is cross-linkable by UV irradiation.

The invention also relates to the use of a modified allophanate according to the invention for preparing a hydrophobic coating composition, in particular a cross-linkable hydrophobic coating composition, notably a hydrophobic coating composition which is cross-linkable by UV irradiation.

The particular, advantageous or preferred features of the modified allophanate according to the invention are particular, advantageous or preferred features of the preparation of a coating composition, notably a hydrophobic coating composition. The same applies for the preparation of a cross-linkable hydrophobic coating composition, notably cross-linkable by UV irradiation.

The different aspects and the advantageous properties of the invention may be illustrated by the examples which follow. These examples are not a limitation of the scope of the invention.

EXAMPLES

The following products are used.

HDI: hexamethyldiisocyanate—Vencorex

Tolonate™ HDB: hexamethylenediisocyanate biuret—Vencorex

NCO equivalent weight=191 g

Viscosity=9,000 mPa·s

Dry extract=100%

Tolonate™ IDT 70 B: a trimer of isophorone diisocyanate—Vencorex

NCO equivalent weight=342 g

Viscosity=600 mPa·s

Dry extract=70%

(Pentaerythritol)tri-acrylate: reaction product of acrylic acid and pentaerythritol Content of OH groups=149 mg KOH/g.

Hexanediol diacrylate (HDDA): an acrylated reactive diluent—Sartomer

An ethoxylated $C_{12}$-$C_{18}$ alcohol with OH content equal to 170 mg KOH/g (RNCAS=68213-23-0)

Catalyst K KAT XK-629: a 20% solution in bismuth tris(2-ethylhexanoate) 2-ethylhexanol.

Example 1: Preparation of an Allophanate of Formula (I)

In a perfectly stirred jacketed reactor, we introduce:

425 g of HDI (2.53 mol) and then 82 g of an ethoxylated $C_{12}$-$C_{18}$ alcohol (0.23 mol) preheated to 40° C.+1.45 g of a butanol-1/butanol-2 mixture (75/25 as a mass ratio m/m) and 5.85 g of catalyst K KAT XK-629 at room temperature. The medium is heated in order to attain the temperature of 110° C. in 2 hours. The reaction medium is held at this temperature for about 1.5 hours.

The NCO content of the reaction medium is regularly measured by a return dibutylamine assay method.

The reaction is stopped by adding 0.066 g of para-toluene sulfonic acid when the NCO content of the reaction medium corresponds to the expected theoretical content.

After 15 minutes, the temperature of the reaction medium is brought back to room temperature.

The NCO content of the final reaction medium is 0.829 mol of NCO for 100 g.

It is then proceeded with 2 successive distillations on a thin film evaporator in vacuo (about 0.5 mbars) at a temperature of 130° C. for removing most of the monomer which has not reacted.

The obtained amount after distillation is 192 g. This corresponds to a yield of the order of 40%.

The final allophanate of formula (I) is characterized by the following data:

NCO content: 0.30 mol of NCO for 100 g, i.e. a weight percent of 12.6%;

viscosity measured at 25° C.: 138 mPa·s.

Example 2: Preparation of a Modified Allophanate According to the Invention

In a three-neck flask equipped with a cooling system, with a mechanical stirrer and with a nitrogen supply, 80 g (0.205 mol) of (pentaerythritol)tri-acrylate (PETIA), 0.02 g of dibutyltin dilaurate (DBTL), 0.072 g of butylhydroxytoluene (BHT) and 100 g of dry toluene are introduced.

61.4 g of allophanate (0.185 mol) of formula (I) of Example 1 is then added with stirring and dropwise and the reaction medium is then heated up to a temperature of 60° C.

The reaction is stopped after 7 h when the NCO groups have entirely reacted and the reaction medium is left to return to room temperature.

The solvent is then evaporated in vacuo.

Comparative Examples 3 to 5

The same synthesis procedure is repeated by using as a comparison the polyisocyanates according to Table 1.

TABLE 1

| Comparative Example | Initial isocyanate | isocyanate (g) | PETIA (g) | toluene (g) | DBTL (g) | Reaction time |
|---|---|---|---|---|---|---|
| 3 | Tolonate IDT 70 B | 63 | 80 | 100 | 0.02 | >24 h |
| 4 | Tolonate HDB | 35.2 | 80 | 1400 | 0.02 | 7 h 30 mins |
| 5 | HDI | 14.2 | 80.3 | 80 | 0.02 | 7 h |

The characteristics of the obtained products are shown in table 2.

TABLE 2

| Example | Initial isocyanate | Content of OH groups (mg KOH/g) | Dry extract (%) | Mn (g/mol) Mw (g/mol) | Viscosity (Pa·s) |
|---|---|---|---|---|---|
| 2 | Allophanate of Example 1 | 41 | 97.6 | 1100 1200 | 17.1 to 23° C. |
| 3 | Tolonate IDT 70 B | 13 | 56.1 | 1300 3100 | 20 to 50° C. |
| 4 | Tolonate HDB | 17 | 63.9 | 1400 5800 | 78 to 50° C. |
| 5 | HDI | 56 | 97.9 | 800 1100 | 24.3 to 23° C. |

The use of the allophanate of Example 1 as an initial reagent gives the possibility of obtaining products with lower viscosity both as compared with isocyanates (HDI) and with known polyisocyanates like the products Tolonate IDT 70 B or Tolonate HDB (Table 2).

Examples 6 to 8: Producing Coatings from Products of Examples 2, 3, 4

The products of Examples 2, 3 and 4 were used for producing a coating which is crosslinkable under UV light under the conditions shown in table 3.

The formulations based on urethane acrylates are adjusted to 50% of dry extract with acetone and 4% of a photoinitiator (Irgacure 500) is then added.

The application is carried out on polycarbonate plates with a K-bar of 12 μm. After evaporation of the solvents (30 minutes at 60° C. in an oven), the plates are stored for 24 h under constant temperature and humidity conditions (50% RH, 23° C.). The thickness of the coating is then 6 μm.

The plates are then cross-linked under UV radiation (mercury lamp) under the conditions shown in Table 3.

TABLE 3

| Running speed | UV-C Dose J/cm² | UV-B Dose J/cm² | UV-A Dose J/cm² | UV-V Dose J/cm² |
|---|---|---|---|---|
| 3 × 5 m/min | 0.213 | 1.41 | 2.148 | 1.917 |

The evaluation of the following properties is carried out 24 h after cross-linking.

Glossiness

It is measured according to an angle of 20° initially and after 50 round-trips with the glass wool ballasted with a weight of 385 g so as to evaluate damage of the surface due to friction.

Contact Angle

The measurement of the angle formed by a drop of water in contact with the coating is an indication of hydrophobicity of the coating. The higher the angle, the more hydrophobic is the surface.

Pencil Hardness

The coating is scratched with graphite leads of increasing hardness according to the scale of FIG. 1.

TABLE 4

| Example | Product (initial isocyanate) | Pencil hardness | Contact angle with water | Initial glossiness (20°) | Glossiness (20°) after 50 rubs |
|---|---|---|---|---|---|
| 6 | Example 2 (The allophanate of Example 1) | 5H-6H | 73 | 90 | 88 |

TABLE 4-continued

| Example | Product (initial isocyanate) | Pencil hardness | Contact angle with water | Initial glossiness (20°) | Glossiness (20°) after 50 rubs |
|---|---|---|---|---|---|
| 7 | Example 3 (Tolonate IDT 70 B) | 3H-4H | 65 | 90 | 86 |
| 8 | Example 4 (Tolonate HDB) | 3H-4H | 50 | 76 | 89 |

The retained hardness is the one for which there was no mark on the coating.

The obtained results show that the application of the allophanate of formula (I) according to Example 1 during the preparation and the application of a modified allophanate according to the invention gives the possibility of obtaining hydrophobic and scratch-resistant coatings.

Examples 9 to 10: Producing Coatings from Products of Examples 2 and 5

The products of Examples 2 and 5 are formulated according to Table 5.

TABLE 5

| Product (initial isocyanate) | Example 9 | Example 10 |
|---|---|---|
| Example 5 (HDI) | 10 | — |
| Example 2 (Allophanate of Example 1) | — | 10 |
| Hexanediol diacrylate (HDDA) | 2.5 | 2.5 |
| Irgacure 500 | 0.25 | 0.25 |

These formulations were then applied on the glass or steel plates according to the test with a K-bar. The dry thickness is 35 μm.

UV irradiation is carried out by means of a mercury lamp according to the conditions of Table 6.

TABLE 6

| Running rate | Total UV dose |
|---|---|
| 2 × 5 m/min | 1234 mW/cm² |

The formulation comprising the product of Example 2 (stemming from the allophanate of Example 1) has the same hardness and aspect characteristics as the Comparative Example but has superior flexibility during the Erichsen indentation test (ISO 1520-1999) (Table 7).

TABLE 7

| Product | Example 9 Example 5 (HDI) | Example 10 Example 2 (Allophanate of Example 1) |
|---|---|---|
| Flexibility - Erichsen indentation (mm) | 0.3 | 1.4 |
| Glossiness (20° C.) | 82 | 85 |
| MEK resistance (double rubs) | >250 | >250 |
| Pencil hardness | 9H | 9H |

The invention claimed is:

1. A hydrophobic modified allophanate, prepared according to a method consisting of (a) providing;
an allophanate of formula (I)

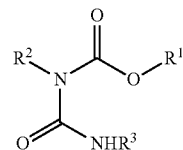

wherein
$R^1$ is the radical of a monoalcohol compound selected from the group consisting of the compound CAS RN 68213-23-0, the compound CAS RN 68154-96-1 and the compound CAS RN 68439-49-6 which is used alone or in mixtures and comprises an ether or polyether function after reaction of the hydrogen of the OH function of the monoalcohol with a compound with an isocyanate function;
$R^2$ and $R^3$, either identical or different, are an aliphatic hydrocarbon group comprising a derivatized or non-derivatized isocyanate function; and then
(b) reacting the allophanate with at least one ester, wherein the ester:
being hydroxy-functionalized;
comprising at least one acrylate function; and
being prepared by reacting an acid selected from the group consisting of acrylic acid and methacrylic acid with at least one alcohol.

2. The hydrophobic modified allophanate according to claim 1, wherein the molar ratio of the urethane/allophanate functions (NCO functionality) is equal to 2.

3. The hydrophobic modified allophanate according to claim 1, wherein the allophanate of formula (I) has an NCO functionality selected from the group consisting of an NCO functionality ranging from 1.9 to 2.3: an NCO functionality ranging from 1.9 to 2.2: an NCO functionality ranging from 1.9 to 2.1; an NCO functionality ranging from 2 to 2.3; and an NCO functionality ranging from 2 to 2.2.

4. The hydrophobic modified allophanate according to claim 1 wherein the allophanate of formula (I) is a homo-allophanate, $R^2$ and $R^3$ being identical, or wherein the allophanate of formula (I) is a mixed allophanate, $R^2$ and $R^3$ being different.

5. The hydrophobic modified allophanate according to claim 1 wherein the allophanate of formula (I) is selected from the group consisting of bis-allophanate and tris-allophanate.

6. The hydrophobic modified allophanate according to claim 1, wherein the allophanate of formula (I) is prepared from hexamethylene diisocyanate (HDI) or isophorone diisocyanate (IPDI).

7. The hydrophobic modified allophanate according to claim 1 wherein the allophanate of formula (I) is prepared from at least one other polyfunctional isocyanate.

8. The hydrophobic modified allophanate according to claim 1, wherein the allophanate of formula (I) is prepared from at least one other polyfunctional isocyanate tricondensate.

9. The hydrophobic modified allophanate according to claim 1, wherein the allophanate of formula (I) is prepared from at least one other polyfunctional isocyanate tricondensate, in a proportion of less than 10% by mass; in a proportion of less than 8% by mass based on the allophanate of formula (I); in a proportion of less than 6% by mass based on the allophanate of formula (I); or in a proportion of less than 2% by mass based on a mixture in preparation of the allophanate of formula (I).

10. The hydrophobic modified allophanate according to claim 1, wherein step (b) is carried out with at least one monohydroxy-functionalized ester.

11. The hydrophobic modified allophanate according to claim 1, wherein step (b) is carried out with a single ester or with two esters.

12. The hydrophobic modified allophanate according to claim 1, wherein step (b) is carried out with at least one alcohol not comprising any oxyalkylene or (poly)oxyalkylene group.

13. The hydrophobic modified allophanate according to claim 1, wherein step (b) applies an ester prepared from an alcohol selected from the compounds of formula (III)

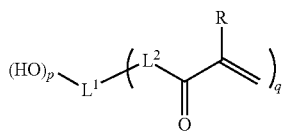

wherein
p is 1, 2, 3, 4 or 5;
$L^1$ is a linear or branched hydrocarbon radical, or a linear or branched radical comprising a hydrocarbon chain and at least one heteroatom;
$L^2$ is O, S or a group of formula NT wherein T is H or a linear or branched $C_1$-$C_8$-alkyl group and N represents a nitrogen atom;
R, either identical or different, is H or a linear or branched $C_1$-$C_8$-alkyl group;
q is 1, 2, 3, 4 or 5.

14. The hydrophobic modified allophanate according to claim 1, wherein the at least one ester is selected from the group consisting of 2-hydroxyalkyl(meth)acrylates, 2-hydroxyethyl(meth)acrylate, 2-hydroxy propyl(meth)acrylate, 3-hydroxypropyl-(meth)acrylate, 4-hydroxybutyl(meth)acrylate, 3-hydroxy-2,2-dimethylpropyl-(meth)acrylate, 2-hydroxyethyl acrylate, 2-hydroxypropyl acrylate, a caprolactone modified by esterification with hydroxyalkyl(meth)acrylates, an ε-caprolactone modified by esterification with hydroxyalkyl(meth)acrylates, an ε-caprolactone modified by esterification with hydroxyalkylacrylates, an ε-caprolactone modified by esterification with 2-hydroxyalkyl(meth)acrylates, an ε-caprolactone modified by esterification with 2-hydroxyalkylacrylates caprolactone triacrylate, glycerol di(meth)acrylate, trimethylolpropane di(meth)acrylate, pentaerythritol tri(meth)acrylate (PETIA), di(pentaerythritol) penta(meth)acrylate, and trimethylolpropane diacrylate.

15. The hydrophobic modified allophanate according to claim 1, wherein the reaction (b) is carried out with at least one ester selected from the group consisting of pentaerythritol triacrylate (PETIA), dipentaerythritol pentaacrylate (DPHA), and trimethylolpropane diacrylate.

16. A of preparation of a coating composition, the method consisting of preparing the modified allophanate according to claim 1 by reacting the allophanate in (a) with the ester in (b).

17. A method of preparation of a hydrophobic coating composition, the method consisting of preparing the modified allophanate of claim 1 by reacting the allophanate in (a) with the ester in (b).

18. The method of preparation according to claim 16 wherein the coating composition is a cross-linkable coating composition.

19. The method of preparation according to claim 16 wherein the coating composition is a coating composition which is cross-linkable by UV irradiation.

20. The method of preparation according to claim 17 wherein the hydrophobic coating composition is a cross-linkable hydrophobic coating composition.

21. The method of preparation according to claim 17 wherein the hydrophobic coating composition is a hydrophobic coating composition which is cross-linkable by UV irradiation.

* * * * *